(12) United States Patent  (10) Patent No.: US 7,030,372 B2
Miller et al.  (45) Date of Patent: Apr. 18, 2006

(54) MICROMACHINED FIELD ASYMMETRIC ION MOBILITY FILTER AND DETECTION SYSTEM

(75) Inventors: Raanan A. Miller, Newton, MA (US); Erkinjon G. Nazarov, Lexington, MA (US)

(73) Assignee: Sionex Corporation, Waltham, MA (US)

( * ) Notice: Subject to any disclaimer, the term of this patent is extended or adjusted under 35 U.S.C. 154(b) by 0 days.

(21) Appl. No.: 10/866,645

(22) Filed: Jun. 10, 2004

(65) Prior Publication Data

US 2005/0023457 A1 Feb. 3, 2005

Related U.S. Application Data

(63) Continuation of application No. 10/321,822, filed on Dec. 16, 2002, now Pat. No. 6,806,463, which is a continuation-in-part of application No. 09/358,312, filed on Jul. 21, 1999, now Pat. No. 6,495,823.

(51) Int. Cl.
    *H01J 49/40* (2006.01)

(52) U.S. Cl. ............... 250/287; 250/288; 250/286; 250/282; 250/290; 250/292

(58) Field of Classification Search ............... 250/288, 250/287, 286, 281, 290, 292
    See application file for complete search history.

(56) References Cited

U.S. PATENT DOCUMENTS

| 2,615,135 A | 10/1952 | Glenn |
| 3,511,986 A | 5/1970 | Llewellyn |
| 3,621,240 A | 11/1971 | Cohen et al. |
| 3,931,589 A | 1/1976 | Aisenberg et al. |
| 4,025,818 A | 5/1977 | Giguere et al. |
| 4,201,921 A | 5/1980 | McCorkle |
| 5,218,203 A | 6/1993 | Eisele |
| 5,420,424 A | 5/1995 | Carnahan et al. |
| 5,455,417 A | 10/1995 | Sacristan |
| 5,479,815 A | 1/1996 | White et al. |
| 5,508,204 A | 4/1996 | Norman |
| 5,536,939 A | 7/1996 | Freidhoff et al. |
| 5,654,544 A | 8/1997 | Dresch |
| 5,723,861 A | 3/1998 | Carnahan et al. |

(Continued)

FOREIGN PATENT DOCUMENTS

DE  4134212 A1  4/1993

(Continued)

OTHER PUBLICATIONS

" A New Method of Separation of Multi-atomic Ions by Mobility at Atmospheric Pressure Using High-Frequency Amplitude-Asymmetric Strong Electric Field", by Buryakov et al., Journal of Mass Spectrometry and Ion Processes, 128, pp 143-148, (1993).*

(Continued)

*Primary Examiner*—Nikita Wells
*Assistant Examiner*—Zia R. Hashmi
(74) *Attorney, Agent, or Firm*—Fish & Neave IP Group Ropes & Gray LLP

(57) ABSTRACT

A micromechanical field asymmetric ion mobility filter for a detection system includes a pair of spaced substrates defining between them a flow path between a sample inlet and an outlet; an ion filter disposed in the path and including a pair of spaced filter electrodes, one electrode associated with each substrate; and an electrical controller for applying a bias voltage and an asymmetric periodic voltage across the ion filter electrodes for controlling the paths of ions through the filter.

91 Claims, 13 Drawing Sheets

U.S. PATENT DOCUMENTS

| | | | |
|---|---|---|---|
| 5,763,876 | A | 6/1998 | Pertinarides |
| 5,789,745 | A | 8/1998 | Martin et al. |
| 5,801,379 | A | 9/1998 | Kouznetsov |
| 5,834,771 | A | 11/1998 | Yoong |
| 5,838,003 | A | 11/1998 | Bertsch et al. |
| 5,869,344 | A | 2/1999 | Linforth et al. |
| 5,965,882 | A | 10/1999 | Megerie et al. |
| 6,066,848 | A | 5/2000 | Kassel et al. |
| 6,124,592 | A | 9/2000 | Spangler |
| 6,180,414 | B1 | 1/2001 | Katzman |
| 6,323,482 | B1 | 11/2001 | Clemmer et al. |
| 6,495,823 | B1 | 12/2002 | Miller et al. |
| 6,498,342 | B1* | 12/2002 | Clemmer .................. 250/287 |
| 6,504,149 | B1 | 1/2003 | Guevremont et al. |
| 6,509,562 | B1 | 1/2003 | Yang et al. |
| 6,512,224 | B1 | 1/2003 | Miller et al. |
| 6,540,691 | B1 | 4/2003 | Phillips |
| 6,621,077 | B1 | 9/2003 | Guevremont et al. |
| 6,639,212 | B1 | 10/2003 | Guevremont |
| 6,653,627 | B1 | 11/2003 | Guevremont |
| 6,690,004 | B1 | 2/2004 | Miller et al. |
| 6,703,609 | B1 | 3/2004 | Guevremont |
| 6,713,758 | B1 | 3/2004 | Guevremont |
| 6,727,496 | B1 | 4/2004 | Miller et al. |
| 6,744,043 | B1 | 6/2004 | Loboda |
| 6,753,522 | B1 | 6/2004 | Guevremont |
| 6,770,875 | B1 | 8/2004 | Guevremont |
| 6,774,360 | B1 | 8/2004 | Guevremont |
| 6,787,765 | B1 | 9/2004 | Guevremont |
| 6,799,355 | B1 | 10/2004 | Guevremont |
| 6,806,463 | B1 | 10/2004 | Miller et al. |
| 6,806,466 | B1 | 10/2004 | Guevremont |
| 6,815,668 | B1 | 11/2004 | Miller et al. |
| 6,815,669 | B1 | 11/2004 | Miller et al. |
| 6,822,224 | B1 | 11/2004 | Guevremont et al. |
| 6,825,461 | B1 | 11/2004 | Guevremont et al. |
| 2001/0030285 | A1 | 10/2001 | Miller et al. |
| 2002/0070338 | A1 | 6/2002 | Loboda |
| 2002/0134932 | A1 | 9/2002 | Guevremont |
| 2003/0020012 | A1 | 1/2003 | Guevremont et al. |
| 2003/0038235 | A1 | 2/2003 | Guevremont et al. |
| 2003/0052263 | A1 | 3/2003 | Kaufman et al. |
| 2003/0070913 | A1 | 4/2003 | Miller et al. |
| 2003/0089847 | A1 | 5/2003 | Guevremont et al. |
| 2003/0132380 | A1 | 7/2003 | Miller et al. |
| 2004/0094704 | A1 | 5/2004 | Miller et al. |
| 2004/0136872 | A1 | 7/2004 | Miller et al. |
| 2004/0232326 | A1 | 11/2004 | Guevremont et al. |
| 2005/0029449 | A1 | 2/2005 | Miller et al. |
| 2005/0040330 | A1 | 2/2005 | Miller et al. |
| 2005/0051719 | A1 | 3/2005 | Miller et al. |
| 2005/0056780 | A1 | 3/2005 | Miller et al. |
| 2005/0121607 | A1 | 6/2005 | Miller et al. |
| 2005/0133716 | A1 | 6/2005 | Miller et al. |
| 2005/0139762 | A1 | 6/2005 | Miller et al. |
| 2005/0167583 | A1 | 8/2005 | Miller et al. |
| 2005/0173629 | A1 | 8/2005 | Miller et al. |
| 2005/0194527 | A1 | 9/2005 | Guevremont et al. |
| 2005/0194532 | A1 | 9/2005 | Guevremont et al. |

FOREIGN PATENT DOCUMENTS

| | | |
|---|---|---|
| SU | 966583 A | 10/1982 |
| SU | 1337934 A2 | 9/1987 |
| SU | 1627984 A2 | 2/1991 |
| SU | 1412447 A1 | 6/1998 |
| SU | 1485808 A1 | 6/1998 |
| WO | WO-97/38302 | 10/1997 |
| WO | WO-00/08455 | 2/2000 |
| WO | WO-00/08456 | 2/2000 |
| WO | WO-00/08457 | 2/2000 |
| WO | WO-01/08197 A1 | 2/2001 |
| WO | WO-01/22049 A2 | 3/2001 |
| WO | WO-01/35441 A1 | 5/2001 |
| WO | WO 01/69217 A2 | 9/2001 |
| WO | WO-01/69220 A2 | 9/2001 |
| WO | WO-01/69647 A2 | 9/2001 |
| WO | WO-02/071053 A2 | 9/2002 |
| WO | WO-02/083276 | 10/2002 |
| WO | WO-03/005016 | 1/2003 |
| WO | WO-2003/015120 | 2/2003 |
| WO | WO-03/067237 A2 | 8/2003 |
| WO | WO-03/067242 A1 | 8/2003 |
| WO | WO-03/067243 A1 | 8/2003 |
| WO | WO-03/067625 A1 | 8/2003 |
| WO | WO-2004/029603 A2 | 4/2004 |
| WO | WO-2004/029614 A1 | 4/2004 |
| WO | WO-2004/030022 A2 | 4/2004 |
| WO | WO-2004/030023 A2 | 4/2004 |
| WO | WO-2004/030129 A2 | 4/2004 |

OTHER PUBLICATIONS

" Atmospheric Pressure Ion Focusing in High-Field Asymmetric Waveform Ion Mobility Spectrometer", by Guevremont et al., Review of Scientific Instruments, 70, pp. 1370-1383, Feb. 1999.*

"A Micromachined Field Driven Radio Frequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05.

Barnett et al., "Isotope Separation Using High-Field Asymmetric Waveform Ion Mobility Spectrometry," Nuclear Instruments & Methods in Physics Research, 450(1):179-185 (2000).

Buryakov et al., "A new method of separation of multi-atomic ions by mobility at atmospheric pressure using a high-frequency amplitude-asymmetric strong electric field," Inter. J. of Mass Spectrometry and Ion Processes, Elsevier Scientific Pub. Co., Amsterdam, NL,.

Buryakov et al., "Separation of ions according to mobility in a strong AC electric field," Letters to Journal of Technical Physics 17:11-12 (1991).

Buryakov et al., Device and Method for Gas Electrophoresis, Chemical Analysis of Environment, edit. Prof. V. V. Malakhov, Novosibirsk: Nauka, pp. 113-127 (1991).

Carnahan et al., "Field Ion Spectrometry—A New Technology for Cocaine and Heroin Detection," SPIE, 2937:106-119 (1997).

Carnahan et al., "Field Ion Spectrometry—A New Analytical Technology for Trace Gas Analysis," ISA Paper 96-009: 87-96 (1996).

Eieceman et al., "Miniature radio-frequency mobility analyzer as a gas chromatogrphic detector for oxygen-containing volatile organic compounds, pheromones and other insect attractants," Journal of Chromatography, vol. 917, pp. 205-217 (2001).

Guevremont et al., "Atmospheric pressure ion focusing in a high-field asymmetric waveform ion mobility spectrometer," Review of Scientific Instruments 70(2):1370-1383 (1999).

Guevremont et al., "Calculation of Ion Mobilities from Electrospray Ionization High Field Asymmetric Waveform Ion Mobility Spectrometry Mass Spectrometry," Journal of Chemical Physics, 114(23):10270-10277 (2001).

Guevremont et al., "High Field Asymmetric Waveform Ion Mobility Spectrometry-Mass Spectrometry: An Investigation of Leucine Enkephalin Ions Produced by Electrospray Ionization," J. Am. Soc. Mass. Spectrom. 10:492-501 (1999).

Handy et al., "Determination of nanomolar levels of perchlorate in water by ESI-FAIMS-MS," JAAS, 15:907-911 (2000).

Krylov, "A Method of Reducing Diffusion Losses in a Drift Spectrometer," Technical Physics, 44(1):113-116 (1999).

Krylov, "Pulses of Special Shapes Formed on a Capacitive Load," Instruments and Experimental Techniques, 40(5): 628 (1997).

Miller et al., "A MEMS Radio-Frequency Ion Mobility Spectrometer for Chemical Agent Detection," Proceedings of the 2000 Solid State Sensors and Actuators Workshop (Hilton Head, SC, Jun. 2000).

Miller et al., "A MEMS radio-frequency ion mobility spectrometer for chemical vapor detection," Sensors and Actuators, vol. 91, pp. 301-312 (2001).

Miller et al., "A Novel Micromachined High-Field Asymmetric Waveform-Ion Mobility Spectrometer," Sensors and Actuators B, B67(3):300-306 (2000).

Phillips, "Method for the Collection and Assay of Volatile Organic Compounds in Breath," Analytical Biochemistry, 247:272-278 (1997).

Pilzecker et al., "On-Site Investigations of Gas Insulated Substations Using Ion Mobility Spectrometry for Remote Sensing of SF6 Decomposition," IEEE, pp. 400-403 (2000).

Riegner et al., "Qualitative Evaluation of Field Ion Spectrometry for Chemical Warfare Agent Detection," Proceedings of the ASMS Conference on Mass Spectrometry and allied Topics, pp. 473A-473B (1997).

Schneider et al., "High Sensitivity GC-FIS for Simultaneous Detection of Chemical Warfare Agents," Journal of Process Analytical Chemistry, vol. 5, Nos. 3,4, pp. 124-136 (2000).

Shute et al., "Curie-point Pyrolysis Mass Spectrometry Applied to Characterization and Identification of Selected Bacillus Species," J. Gen. Microbiology, 130:343-355 (1984).

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

* cited by examiner

MICROMACHINED FIELD ASYMMETRIC ION MOBILITY FILTER AND DETECTION SYSTEM

CROSS-REFERENCE OF RELATED APPLICATIONS

This application is a continuation of, incorporates by reference in entirety, and claims priority to and benefit of, U.S. patent application Ser. No. 10/321,822, filed on 16 Dec. 2002. U.S. patent application Ser. No. 10/321,822 is a continuation-in-part of, and incorporates by reference in entirety, U.S. application Ser. No. 09/358,312, filed 21 Jul. 1999.

BACKGROUND OF THE INVENTION

This invention relates to a Field Asymmetric Ion Mobility (FAIM) filter, and more particularly, to a micromachined FAIM filter and spectrometer.

The ability to detect and identify explosives, drugs, chemical and biological agents as well as air quality has become increasingly more critical given increasing terrorist and military activities and environmental concerns. Previous detection of such agents was accomplished with conventional mass spectrometers, time of flight ion mobility spectrometers and conventionally machined FAIM spectrometers.

Mass spectrometers are very sensitive, highly selective and provide a fast response time. Mass spectrometers, however, are large and require significant amounts of power to operate. They also require a powerful vacuum pump to maintain a high vacuum in order to isolate the ions from neutral molecules and permit detection of the selected ions, and are also very expensive.

Another spectrometric technique which is less complex is time of flight ion mobility spectrometry which is the method currently implemented in most portable chemical weapons and explosives detectors. The detection is based not solely on mass, but on charge and cross-section of the molecule as well. However, because of these different characteristics, molecular species identification is not as conclusive and accurate as the mass spectrometer. Time of flight ion mobility spectrometers typically have unacceptable resolution and sensitivity limitations when attempting to reduce their size, that is a drift tube length less than 2 inches. In time of flight ion mobility, the resolution is proportional to the length of the drift tube. The longer the tube the better the resolution, provided the drift tube is also wide enough to prevent all ions from being lost to the side walls due to diffusion. Thus, fundamentally, miniaturization of time of flight ion mobility systems leads to a degradation in system performance. While these devices are relatively inexpensive and reliable, they suffer from several limitations. First, the sample volume through the detector is small, so to increase spectrometer sensitivity either the detector electronics must have extremely high sensitivity, requiring expensive electronics, or a concentrator is required, adding to system complexity. In addition, a gate and gating electronics are usually needed to control the injection of ions into the drift tube.

FAIM spectrometry was developed in the former Soviet Union in the 1980's. FAIM spectrometry allows a selected ion to pass through a filter while blocking the passage of undesirable ions. Conventional FAIM spectrometers are large and expensive, e.g., the entire device is nearly a cubic foot in size and costs over $25,000. These systems are not suitable for use in applications requiring small detectors. They are also relatively slow, taking as much as one minute to produce a complete spectrum of the sample gas, are difficult to manufacture and are not mass producible.

SUMMARY OF THE INVENTION

It is therefore an object of this invention to provide a FAIM filter and detection system which can more quickly and accurately control the flow of selected ions to produce a sample spectrum than conventional FAIM devices.

It is a further object of this invention to provide such a filter and detection system which can detect multiple preselected ions without having to sweep the bias voltage.

It is a further object of this invention to provide such a filter and detection system which can even detect selected ions without a bias voltage.

It is a further object of this invention to provide such a filter and detection system which can detect ions spatially based on the ions' trajectories.

It is a further object of this invention to provide such a filter and detection system which has a very high resolution.

It is a further object of this invention to provide such a filter and detection system which can detect selected ions faster than conventional detection devices.

It is a further object of this invention to provide such a filter and detection system which has a sensitivity of parts per billion to parts per trillion.

It is a further object of this invention to provide such a filter and detections system which may be packaged in a single chip.

It is further object of this invention to provide such filter and detection system which is cost effective to implement and produce.

The invention results from the realization that an extremely small, accurate and fast FAIM filter and detection system can be achieved by defining a flow path between a sample inlet and an outlet using a pair of spaced substrates and disposing an ion filter within the flow path, the filter including a pair of spaced electrodes, one electrode associated with each substrate and a controller for selectively applying a bias voltage and an asymmetric periodic voltage across the electrodes to control the path of ions through the filter.

The invention results from the further realization that by providing an array of filters, each filter associated with a different bias voltage, the filter may be used to detect multiple selected ions without sweeping the bias voltage.

The invention results from the realization that by varying the duty cycle of the periodic voltage, no bias voltage is required.

The invention results from the further realization that by segmenting the detector, ion detection may be achieved with greater accuracy and resolution by detecting ions spatially according to the ions' trajectories as the ions exit the filter.

This invention features a micromechanical field asymmetric ion mobility filter for a detection system. There is a pair of spaced substrates defining between them a flow path between a sample inlet and an outlet, an ion filter disposed in the path and including a pair of spaced filter electrodes, one electrode associated with each substrate and an electrical controller for applying a bias voltage and an asymmetric periodic voltage across the ion filter electrodes for controlling the paths of ions through the filter.

In a preferred embodiment there may be a detector, downstream from the ion filter, for detecting ions that exit the filter. The detector may include a plurality of segments, the segments separated along the flow path to spatially separate the ions according to their trajectories. There may be confining electrodes, responsive to the electrical controller, for concentrating selected ions as they pass through the filter. The confining electrodes may be silicon. The silicon electrodes may act as spaces for spacing the substrates. There may be heater for heating the flow path. The heater may include the ion filter electrodes. The electrical controller may include means for selectively applying a current through the filter electrodes to heat the filter electrodes. The substrate may be glass. The glass may be Pyrex®. There may be an ionization source, upstream from the filter, for ionizing a fluid flow from the sample inlet. The ionization source may include a radioactive source. The ionization source may include an ultraviolet lamp. The ionization source may include a corona discharge device. There may be a clean air outlet for introducing purified air into the flow path. There may be a pump in communication with the flow path, for regulating a fluid flow through the flow path.

The invention also features a field asymmetric ion mobility filter and detection system. There is a housing having a flow path between a sample inlet and an outlet, an ion filter disposed in the flow path and including a pair of spaced filter electrodes, an electrical controller for applying a bias voltage and an asymmetric periodic voltage across the ion filter electrodes for controlling the path of ions through the filter, and a segmented detector, downstream from the ion filter, its segments separated along the flow path to spatially separate the ions according to their trajectories.

In a preferred embodiment there may be confining electrodes, responsive to the electrical controller, for concentrating the ions as they pass through the filter. The confining electrode may be silicon. The silicon electrodes may act as a spacer for spacing the filter electrodes. There may be a heater for heating the flow path. The heater may include the ion filter electrodes. The electrical controller may include means for selectively applying current through the filter electrodes to heat the filter electrodes. There may be an ionization source upstream from the filter for ionizing fluid flow from the sample inlet. The ionization source may include a radioactive source. The ionization source may include an ultraviolet lamp. The ionization source may include a coronadischarge device. There may be a clean air inlet for introducing purified air into the flow path. There may be a pump in communication with the flow path for regulating a fluid flow through the flow path.

The invention also features a field asymmetric ion mobility filter array. There is a housing defining at least one flow path between a sample inlet and an outlet, a plurality of ion filters disposed within the housing, each ion filter including a pair spaced filter electrodes, and an electrical controller for applying a bias voltage and an asymmetric periodic voltage across each pair of ion filter electrodes for controller the path of ions through each filter.

In a preferred embodiment each ion filter may be associated with one of the flow paths. There may be a detector downstream from each ion filter for detecting ions that exit each said filter. Each detector may include a plurality of segments, the segments separated along the flow path to spatially separate the ions according to their trajectories. There may be a plurality of confining electrodes, responsive to the electrical controller, for concentrating the ions as they pass through each filter. Each confining electrode may be silicon. The silicon electrode may act as a spacer for spacing the filter electrodes. There may be a heater fro heating the at least one flow path. The heater may include each pair of ion filter electrodes. The electrical controller may include means for selectively applying a current through each pair of filter electrodes to heat the filter electrodes. There may be an ionization source upstream from each filter for ionizing a fluid flow from the sample inlet. The ionization source may be a radioactive source. The ionization source may be an ultraviolet lamp. The ionization source may be a corona discharge device. There may be a clean air inlet for introducing purified air into at least one flow path. There may be a pump in communication with each flow path for regulating a fluid flow through each flow path.

The invention also features an uncompensated field asymmetric ion mobility filter for a detection system. There is a housing having a flow path between a sample inlet and an outlet, an ion filter disposed in the path and including a pair of spaced filter electrodes, an electrical controller for applying an uncompensated asymmetric periodic voltage across the ion filter for controlling the path of ions through the ion filter, and a selection circuit for selectively adjusting the duty cycle of the periodic voltage to target a selected specie or species of ion to be detected.

In a preferred embodiment there may be a detector downstream from the ion filter for detecting ions that exit the filter. The detector may include a plurality of segments, the segments separated along the flow path to spatially separate the ions according to their trajectories. There may be a confining electrode, responsive to the electrical controller, for concentrating the ions as they pass through the filter. The confining electrode may be silicon. The silicon electrode may act as a spacer for spacing the filter electrodes. There may be a heater for heating the flow path. The heater may include the ion filter electrodes. The electrical controller may include means for selectively applying a current through the filter electrodes to heat the filter electrodes. There may be an ionization source, upstream from the filter, for ionizing a fluid flow from sample inlet. The ionization source may include a radioactive source. The ionization source may include an ultraviolet lamp. The ionization source may include a corona discharge device. There may be a clean air inlet for introducing purified air into the flow path. There may be a pump in communication with the flow path for regulating a fluid flow through the flow path.

The invention also features a field asymmetric ion mobility filter. There is a housing having a flow path between a sample inlet and an outlet, an ion filter disposed in the flow path and including a pair of spaced filter electrodes, a pair of confining electrodes transverse to the flow path, and an electrical controller for applying a first bias voltage and an asymmetric periodic voltage across the ion filter electrodes and for applying a second bias voltage across the confining electrodes for controlling the path of ions through the filter.

In a preferred embodiment there may be a detector downstream from the ion filter for detecting ions that exit the filter. The detector may include a plurality of segments, the segments separated along the flow path to spatially separate the ions according to their trajectories. The confining electrodes may be silicon. The silicon electrodes may act as a spacer for spacing the filter electrodes. There may be a heater for heating the flow path. The heater may include the ion filter electrodes. The heater may include the confining electrodes. The electrical controller may include means for selectively applying a current through the filter electrodes to heat the filter electrodes. The electrical controller may include means for selectively applying a current through the confining electrodes to heat the confining electrodes. There may be an ionization source upstream from the filter for ionizing fluid flow from the sample inlet. The ionization source may include a radiation source. The ionization source may include an ultraviolet lamp. The ionization source may be a corona discharge device. There may be a clean air inlet for introducing purified air into the flow path. There may be a pump in communication with the flow path for regulating a fluid flow through the flow path.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

Other objects, features and advantages will occur to those skilled in the art from the following description of a preferred embodiment and the accompanying drawings, in which.

DETAILED DESCRIPTION OF THE INVENTION

A description of preferred embodiments of the invention follows.

Figure 1:
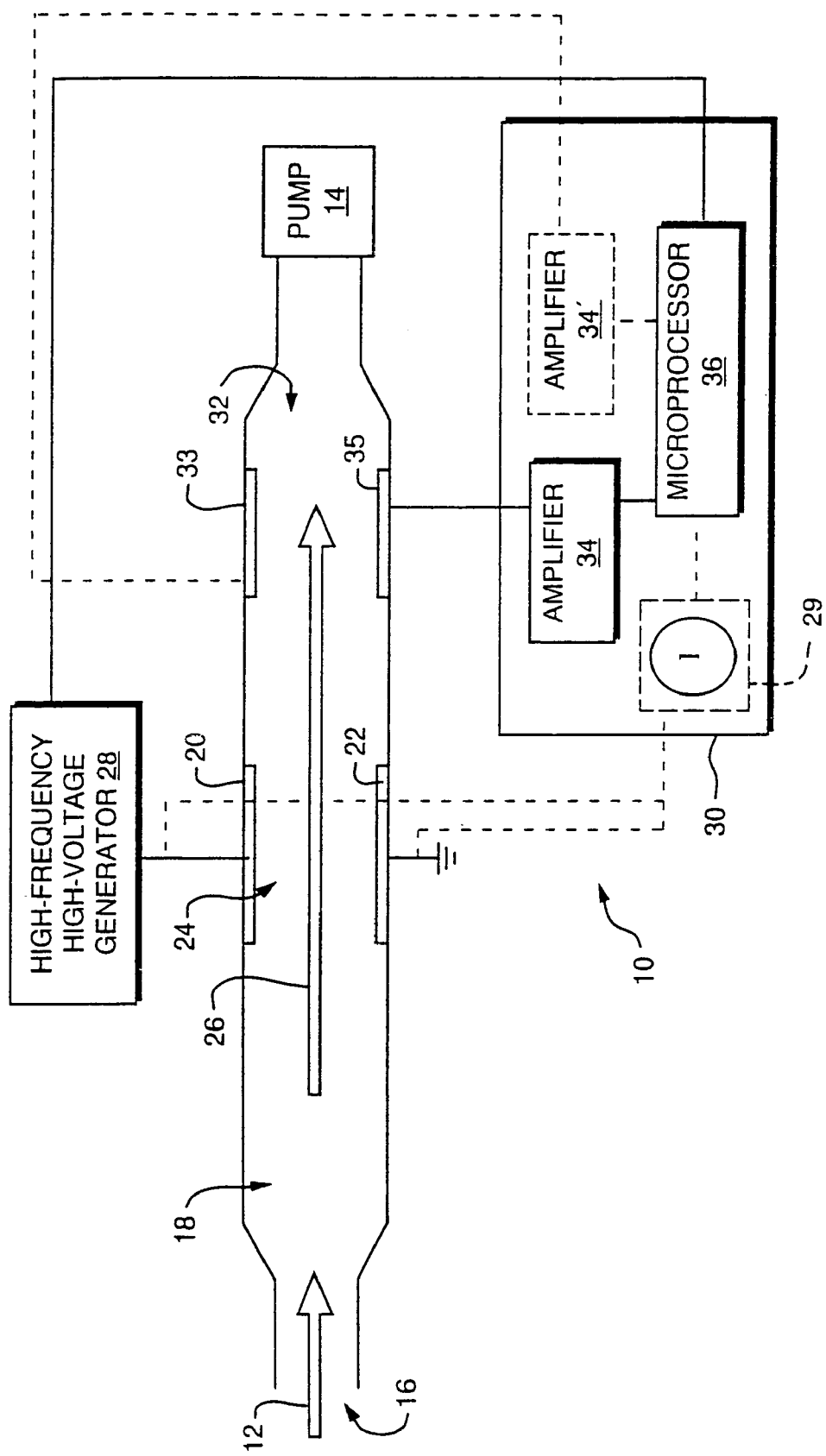
FIG. 1 is a schematic block diagram of the micromachined filter and detection system according to the present invention.

FAIM spectrometer 10, FIG. 1, operates by drawing a gas, indicated by arrow 12, via pump 14, through inlet 16 into ionization region 18. The ionized gas is passed between parallel electrode plates 20 and 22, which comprise ion filter 24, following flow path 26. As the gas ions pass between plates 20 and 22, they are exposed to an asymmetric oscillating electric field between electrode plates 20 and 22 induced by a voltage applied to the plates by voltage generator 28 in response to electronic controller 30

As ions pass through filter 24, some are neutralized by plates 20 and 22 while others pass through and are sensed by detector 32. Detector 32 includes a top electrode 33 at a predetermined voltage and a bottom electrode 35, typically at ground. Top electrode 33 deflects ions downward to electrode 35. However either electrode may detect ions depending on the ion and the voltage applied to the electrodes. Moreover, Multiple ions may be detected by using top electrode 33 as one detector and bottom electrode 35 as a second detector. Electronic controller 30 may include for example, amplifier 34 and microprocessor 36. Amplifier 34 amplifies the output of detector 32, which is a function of the charge collected by detector 34, and provides the output to microprocessor 36 for analysis. Similarly, amplifier 34', shown in phantom, may be provided where electrode 33 is also utilized as a detector.

Figure 2:
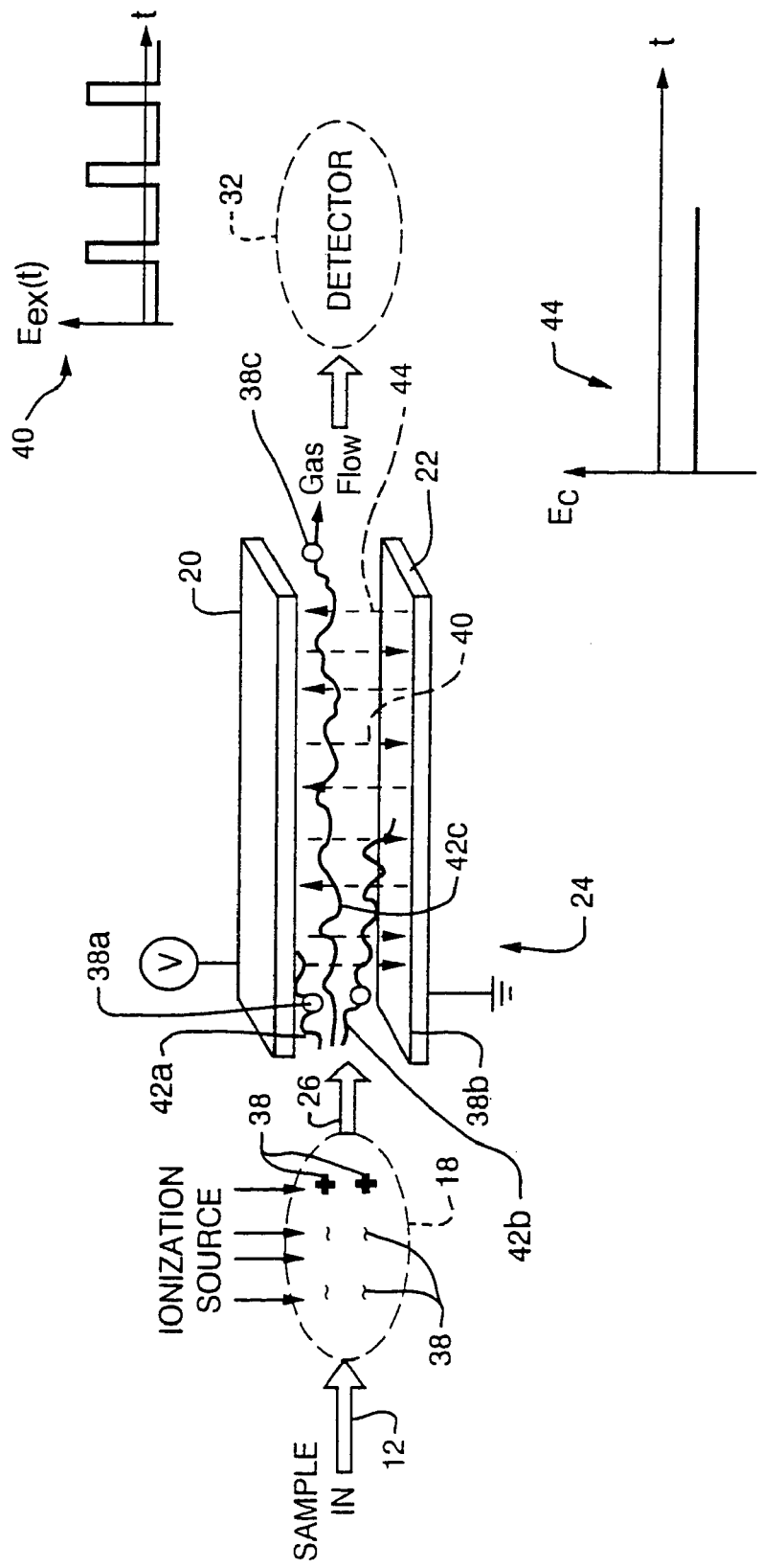
FIG. 2 is a schematic representation of the ions as they pass through the filter electrodes of FIG. 1 toward the detector.

As ions 38, FIG. 2, pass through alternating asymmetric electric field 40, which is transverse to gas flow 12, electric field 40, causes the ions to "wiggle" along paths 42a, 42b and 42c. Field 40 is typically in the range of ±(1000–2000) volts dc and has a maximum field strength of 40,000 V/cm. The path taken by a particular ion is a function of its mass, size, cross-section and charge. Once an ion reaches electrode 20 or 22, it is neutralized. A second, bias or compensation field 44, typically in the range of ±2000 V/cm or ±100 volts dc, is concurrently induced between electrodes 20 and 22 by as bias voltage applied to plates 20 and 22, also by voltage generator 28, FIG. 1, in response to microprocessor 36 to enable a preselected ion species to pass through filter 24 to detector 32. Compensation field 44 is a constant bias which offsets alternating asymmetric field 40 to allow the preselected ions, such as ion 38c to pass to detector 32. Thus, with the proper bias voltage, a particular species of ion will follow path 42c while undesirable ions will follow paths 42a and 42b to be neutralized as they encounter electrode plates 20 and 22.

The output of FAIM spectrometer 10 is a measure of the amount of charge on detector 32 for a given bias voltage 44. The longer filter 24 is set at a given compensation bias voltage, the more charge will accumulate on detector 32. However, by sweeping compensation voltage 44 over a predetermined voltage range, a complete spectrum for sample gas 23 can be achieved. The FAIM spectrometer according to the present invention requires typically less than thirty seconds and as little as one second to produce a complete spectrum for a given gas sample.

Figure 3A:
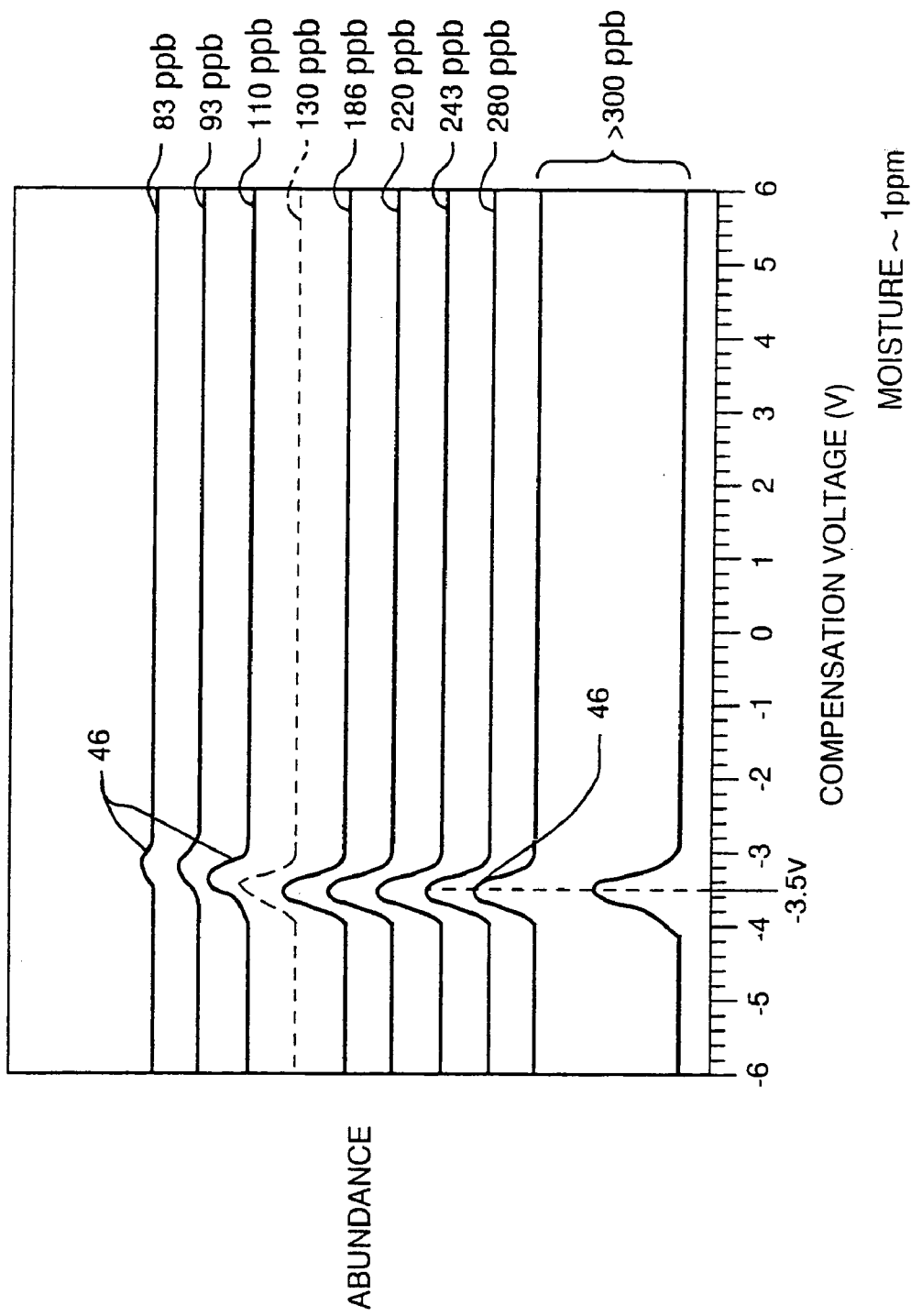
FIG. 3A is a graphical representation of the bias voltage required to detect acetone and the sensitivity obtainable.
Figure 3B:
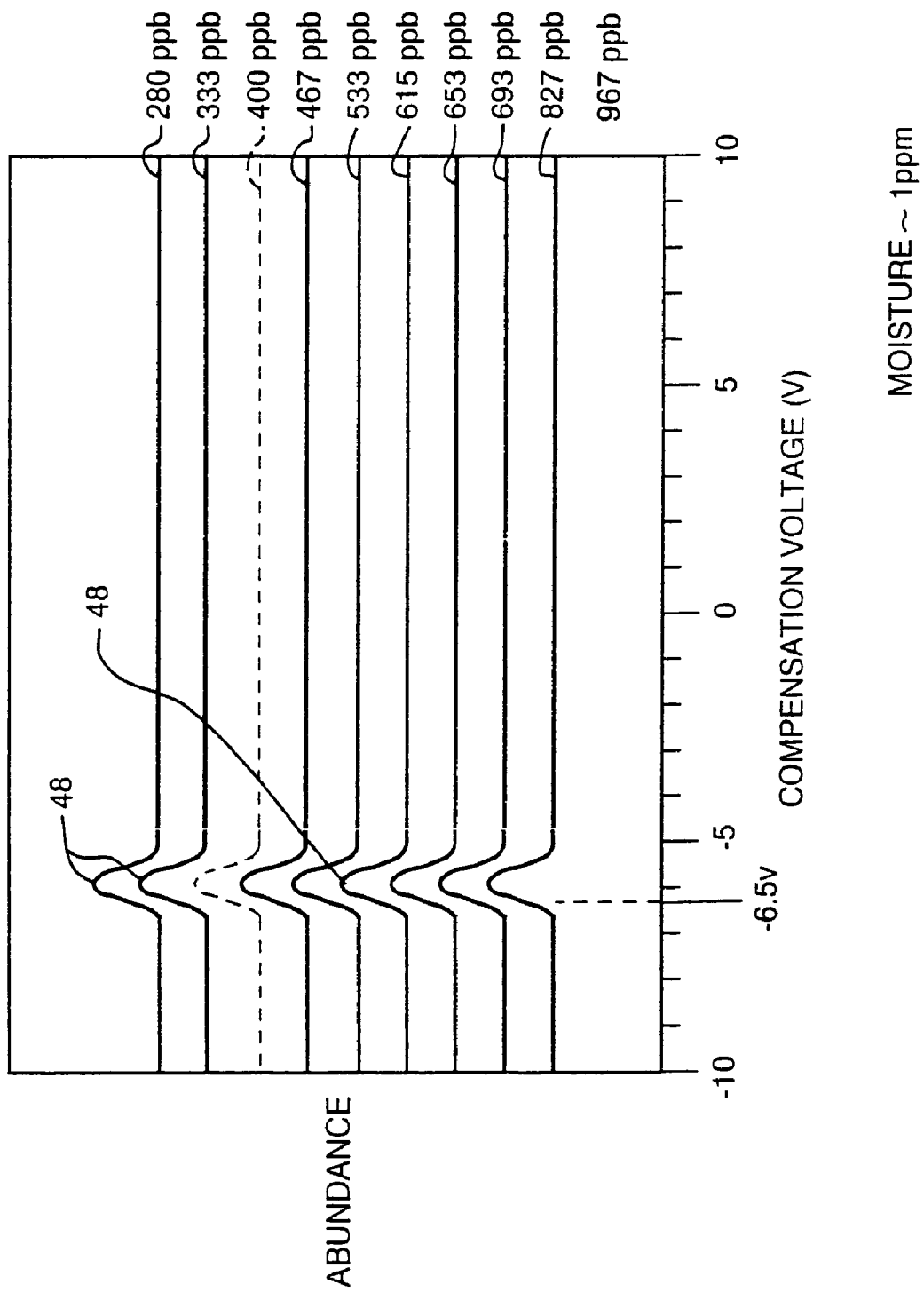
FIG. 3B is a representation, similar to FIG. 3A, of the bias voltage required to detect Diethyl methyl amine.

By varying compensation bias voltage 44 the species to be detected can be varied to provide a complete spectrum of the gas sample. For example, with a bias voltage of −3.5 volts acetone was detected as demonstrated by concentration peaks 46, FIG. 3A in concentrations as low as 83 parts per billion. In contrast, at a bias voltage of −6.5 volts, diethyl methyl amine, peaks 48, FIG. 3B, was detected in concentrations as low as 280 parts per billion.

Figure 4:
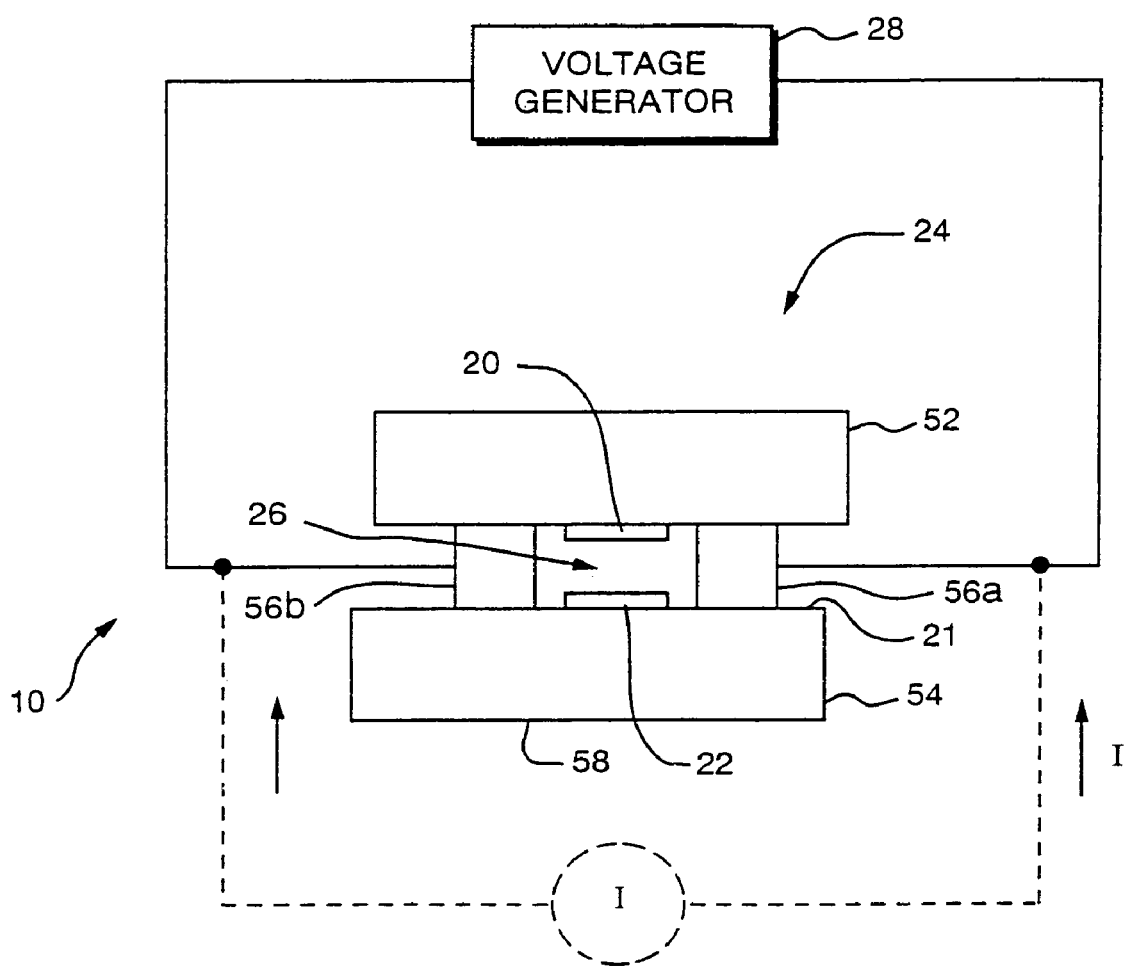
FIG. 4 is a cross sectional of the view of the spaced, micromachined filter according to the present invention.

Filter 24, FIG. 4, is on the order of one inch is size. Spectrometer 10 includes spaced substrates 52 and 54, for example glass such as Pyrex® available from Corning Glass, Corning, N.Y., and electrodes 20 and 22, which may be example gold, titanium, or platinum, mounted or formed on substrates 52 and 54, respectively. Substrates 52 and 54 are separated by spacers 56a and 56b which may be formed by etching or dicing silicon wafer. The thickness of spacers 56a and 56b defines the distance between electrodes 20 and 22. Moreover, applying the same voltage to silicon spacers 56a–b, typically ±(10–1000 volts dc) transforms spacers 56a–b into electrodes which produce a confining electric field 58, which guides or confines the ions' paths to the center of flow path 26. This increases the sensitivity of the system by preserving more ions so that more ions strike detector 34. However, this is not a necessary limitation of the invention.

To maintain accurate and reliable operation of spectrometer 10, neutralized ions which accumulate on electrode plates 20 and 22 must be purged. This may be accomplished by heating flow path 26. For example, controller 30, FIG. 1, may include current source 29, shown in phantom, which provides, in response to microprocessor 36, a current I to electrode plates 20 and 22 to heat the plates, removing accumulated molecules. Similarly, current I may instead be applied to spacer electrodes 56a and 56b, FIG. 4, to heat flow path 26 and clean plates 20 and 22.

Figure 5:
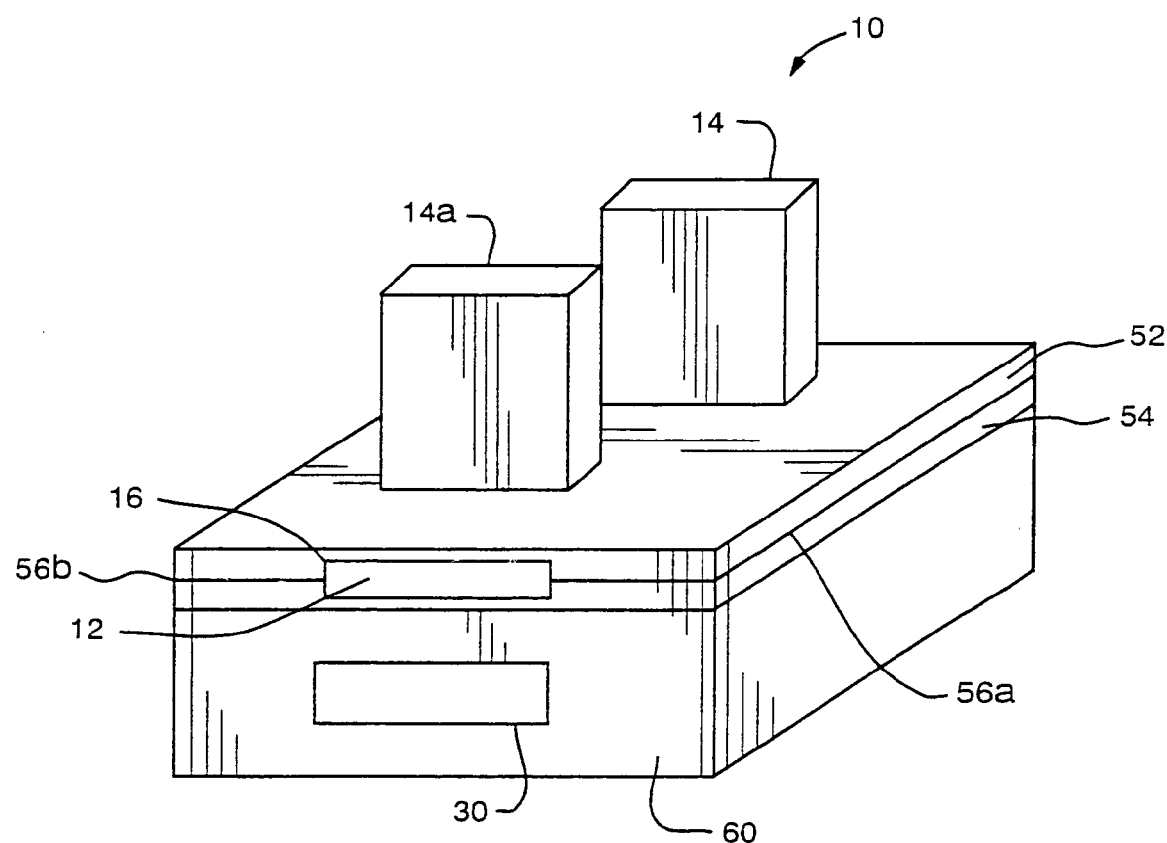
FIG. 5 is a three dimensional view of the packaged micromachined filter and detection system, including fluid flow pumps, demonstrating the miniaturized size which maybe realized.

Packaged FAIM spectrometer 10, FIG. 5, may be reduced in size to one inch by one inch by one inch. Pump 14 is mounted on substrate 52 for drawing a gas sample 12 into inlet 16. Clean dry air may be introduced into flow path 26, FIG. 1, by recirculation pump 14a prior to or after ionization of the gas sample. Electronic controller 30 may be etched into silicon control layer 60 which combines with substrates 52 and 54 to form a housing for spectrometer 10. Substrates 52 and 54 and control layer 60 may be bonded together, for example, using anodic bonding, to provide an extremely small FAIM spectrometer. Micro pumps 14 and 14a provide a high volume thoughput which further expedites the analysis of gas sample 12. Pumps 14 and 14a may be, for example, conventional miniature disk drive motors fitted with small centrifugal air compressor rotors or micromachined pumps, which produce flow rates of 1 to 4 liters per minute. One example of pump 14 is available from Sensidyne, Inc., Clearwater, Fla.

Figure 6:
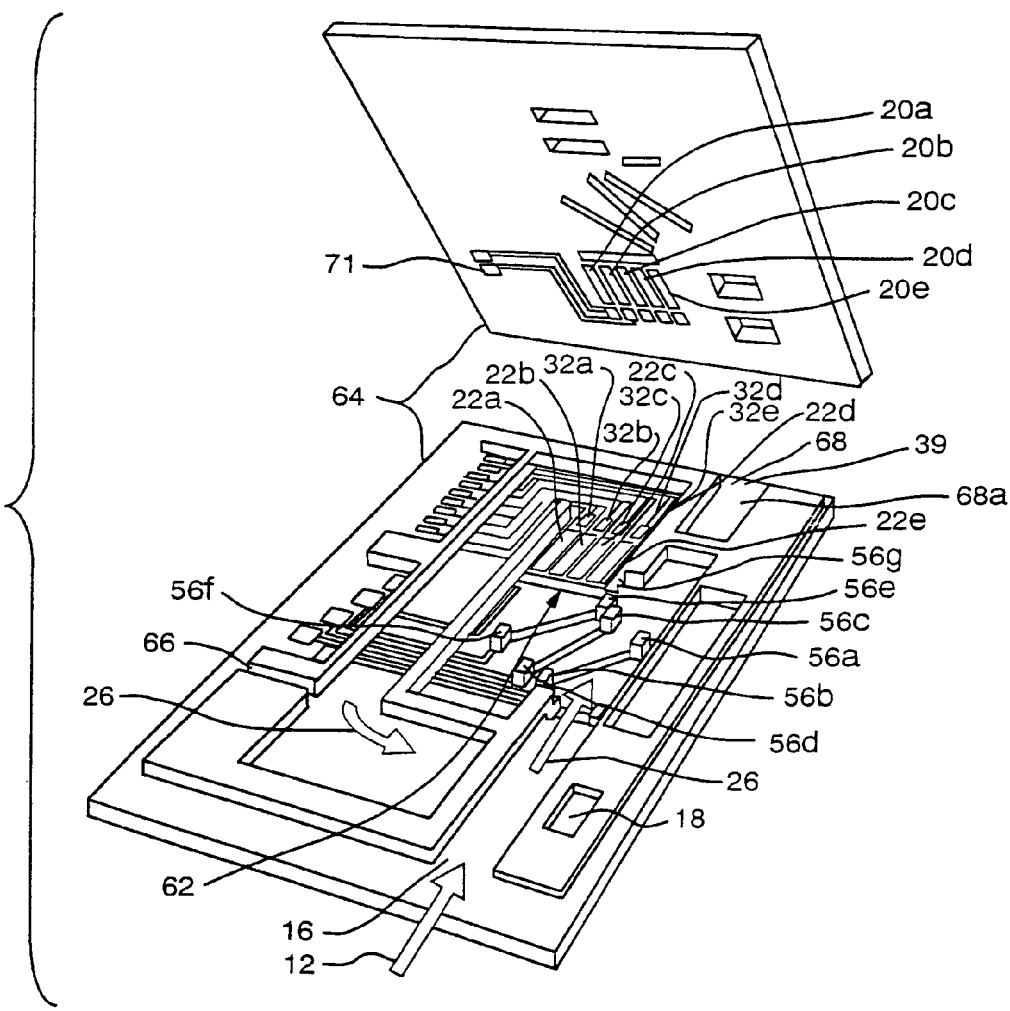
FIG. 6 is an exploded view of one embodiment according to the present invention in which an array of filters and detectors are disposed in a single flow path.

While the FAIM spectrometer according to the present invention quickly produces a spectrum for a particular gas sample, the time for doing so may be further reduced with an array of filters 32. FAIM spectrometer 10, FIG. 6, may include filter array 62, a single inlet 16 and single flow path 26. Sample gas 23 is guided by confining electrodes 56a–h to filter array 62 after passing by ionization source 18, which may include an ultraviolet light source, a radioactive device or corona discharge device. Filter array 62 includes, for example, paired filter electrodes 20a–d and 22a–e and may simultaneously detect different ion species by applying a different compensation bias voltage 44, FIG. 2, to each electrode pair and sweeping each electrode pair over a different voltage range greatly reducing the sweep time. However, array 62 may include any number of filters depending on the size of the spectrometer. Detector array 64, which includes detectors 32a–e, detects multiple selected ion species simultaneously, thereby reduce the time necessary to obtain a spectrum of the gas sample 12. The electrode pairs share the same asymmetric periodic ac voltage 40.

Clean dry air may be introduced into flow path 26 through clean air inlet 66 via recirculator pump 14a, FIG. 5. Drawing in clean dry air assists in reducing the FAIM spectrometer's sensitivity to humidity. Moreover, if the spectrometer is operated without clean dry air and a known gas sample is introduced in the device, the device can be used as a humidity sensor since the resulting spectrum will change with moisture concentration from the standardized spectrum for the given sample.

Figure 7:
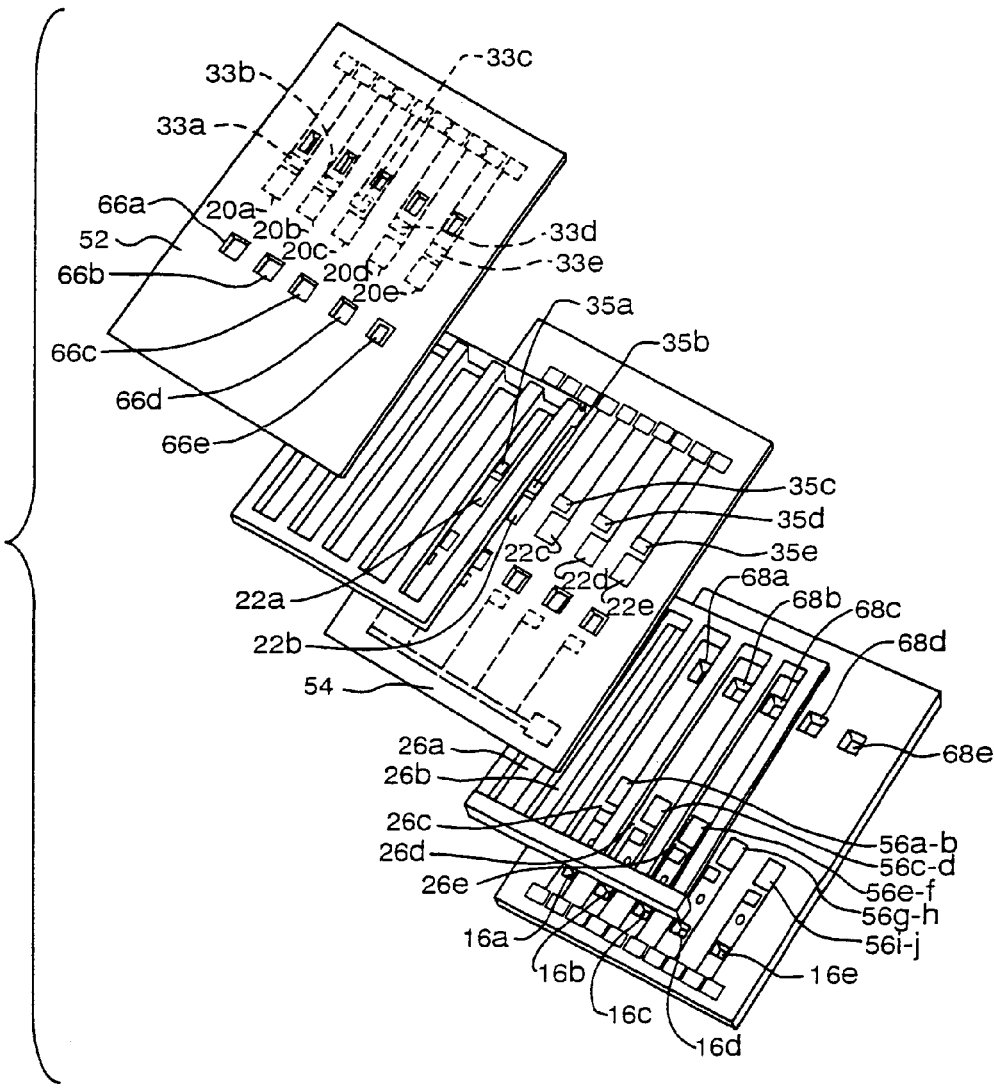
FIG. 7 is an exploded view, similar to FIG. 6, in which the array of filters is stacked and one filter and detector is associated with a single flow path.

However, rather than each filter 32a–e of filter array 62 sharing the same flow path 26, individual flow paths 26a–e, FIG. 7, may be provided so that each flow path has associated with it, for example, inlet 16a, ionization region 18a, confining electrodes 56a', 56b', ion filter electrode pair 20a, 22a, detector electrode pair 33a, 35a, and exit port 68a.

Figure 8:
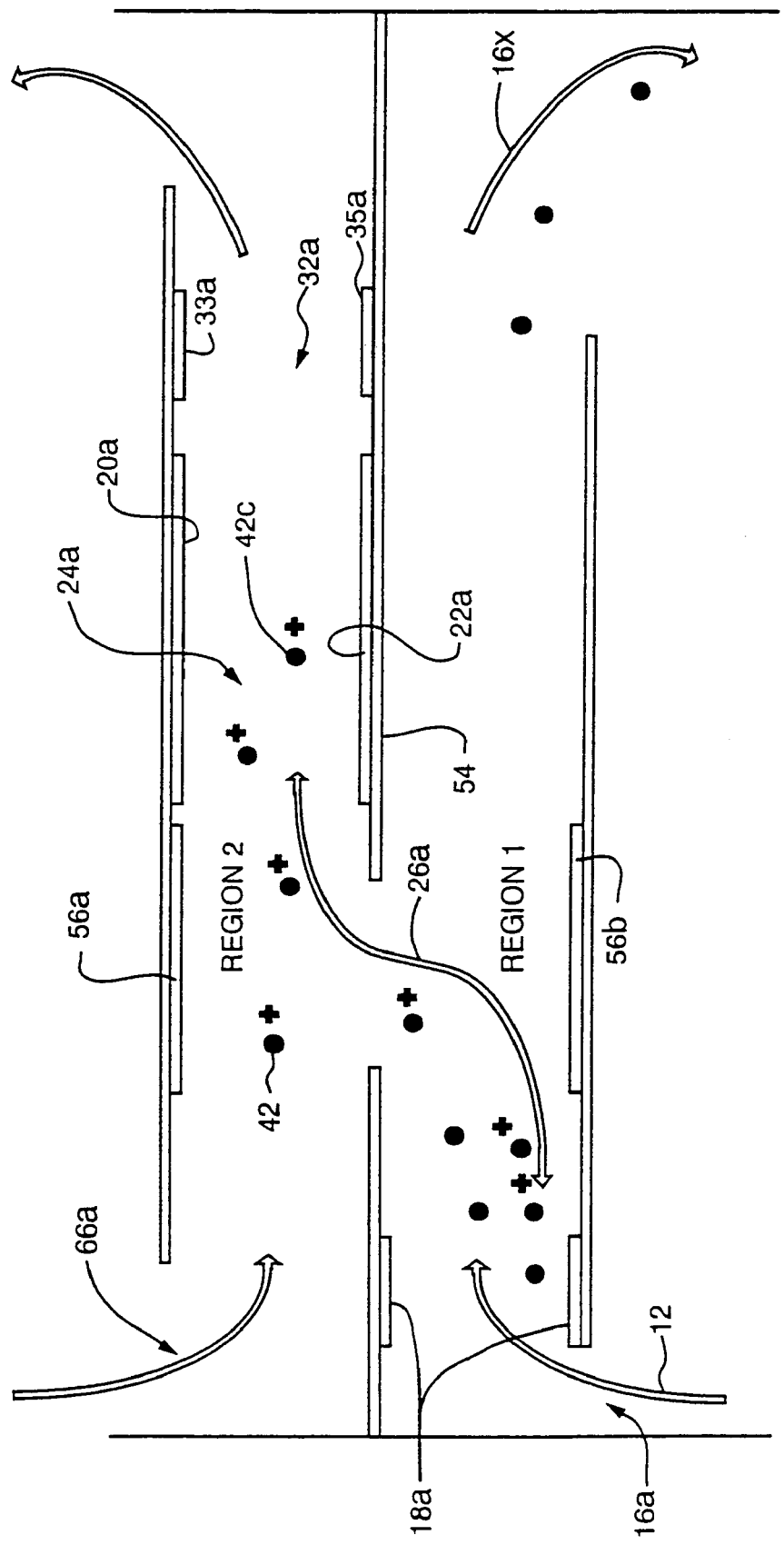
FIG. 8 is a cross sectional representation of a single flow path of the arrayed filter and detector system of FIG. 7.

In operation, sample gas 12 enters sample inlet 16a, FIG. 8, and is ionized by, for example, a corona discharge device 18a. The ionized sample is guided towards ion filter 24a by confining electrodes 56a. As ions pass between ion filter electrodes 20a and 22a, undesirable ions will be neutralized while selected ions will pass through filter 24a to be detected by detector 32a.

Figure 9:
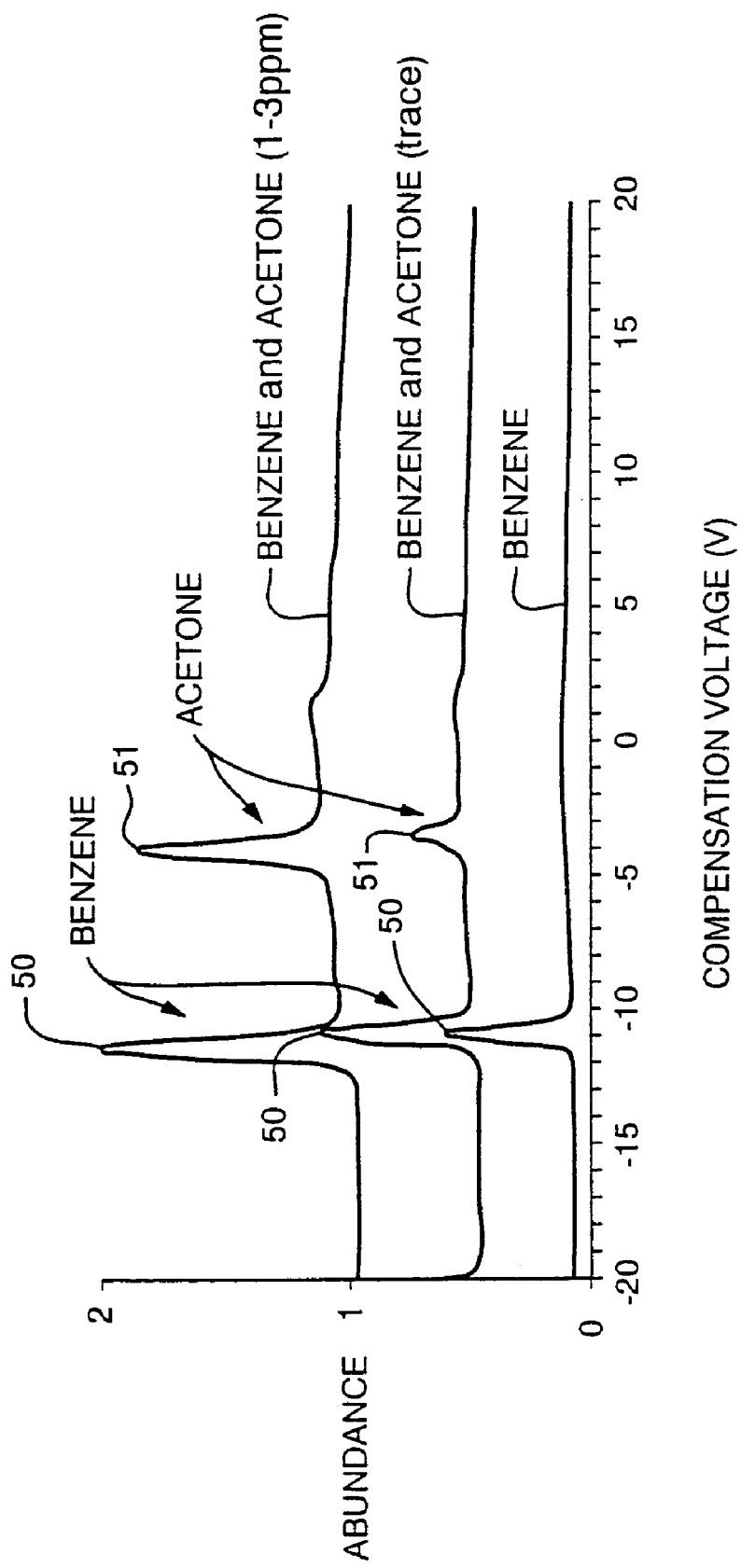
FIG. 9 is a graphical representation demonstrating simultaneous multiple detections of benzene and acetone.

As shown in FIG. 9, multiple, simultaneous detections were made of Benzene, peaks 50 and acetone peaks 51, demonstrating the advantage of the arrayed filters and detectors according to the present invention.

Figure 10:
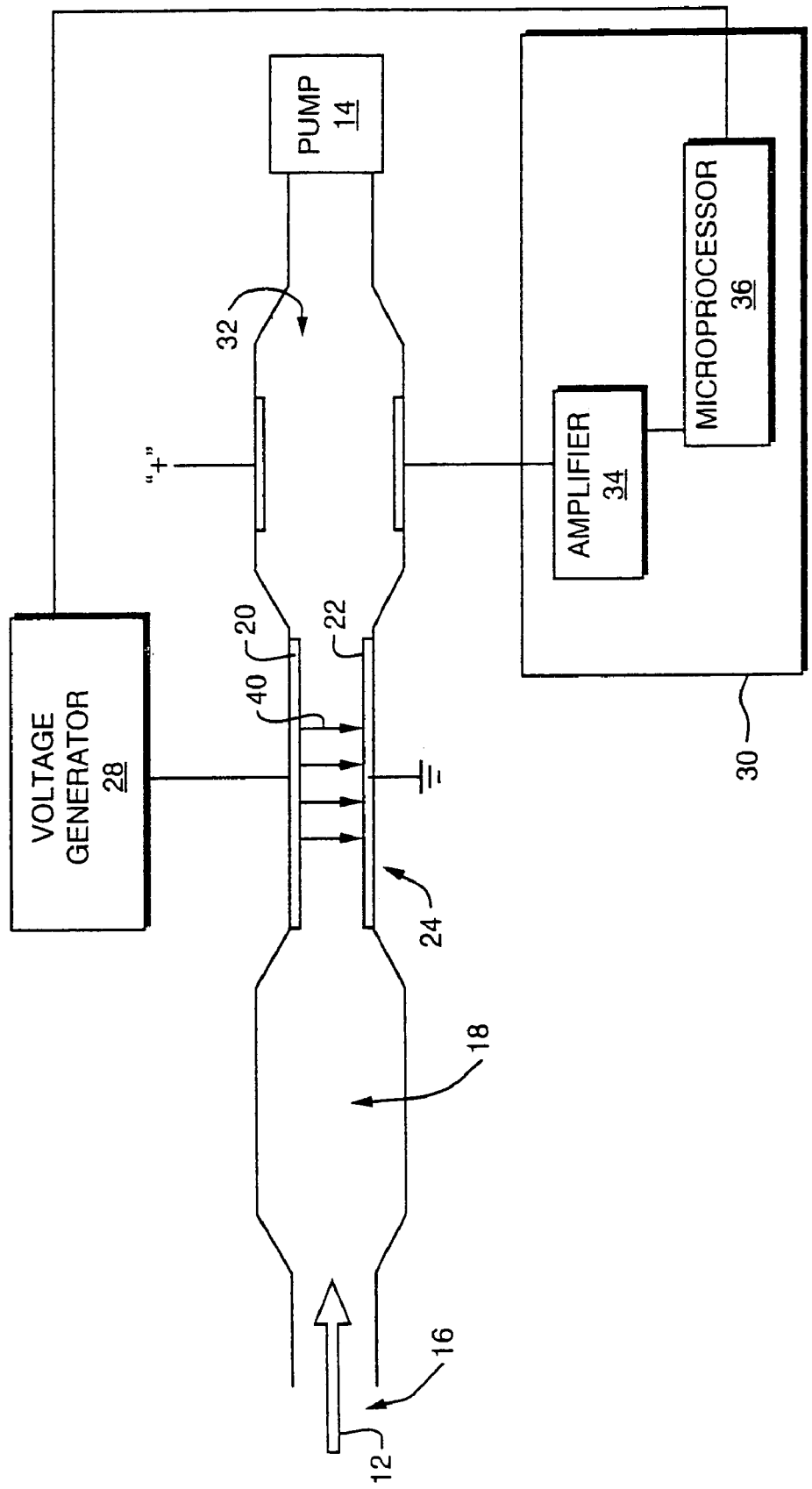
FIG. 10 is a schematic block diagram, similar FIG. 1, in which the filter is not compensated by a bias voltage and the duty cycle of the periodic voltage is instead varied to control the flow of ions through the filter.
Figure 11:
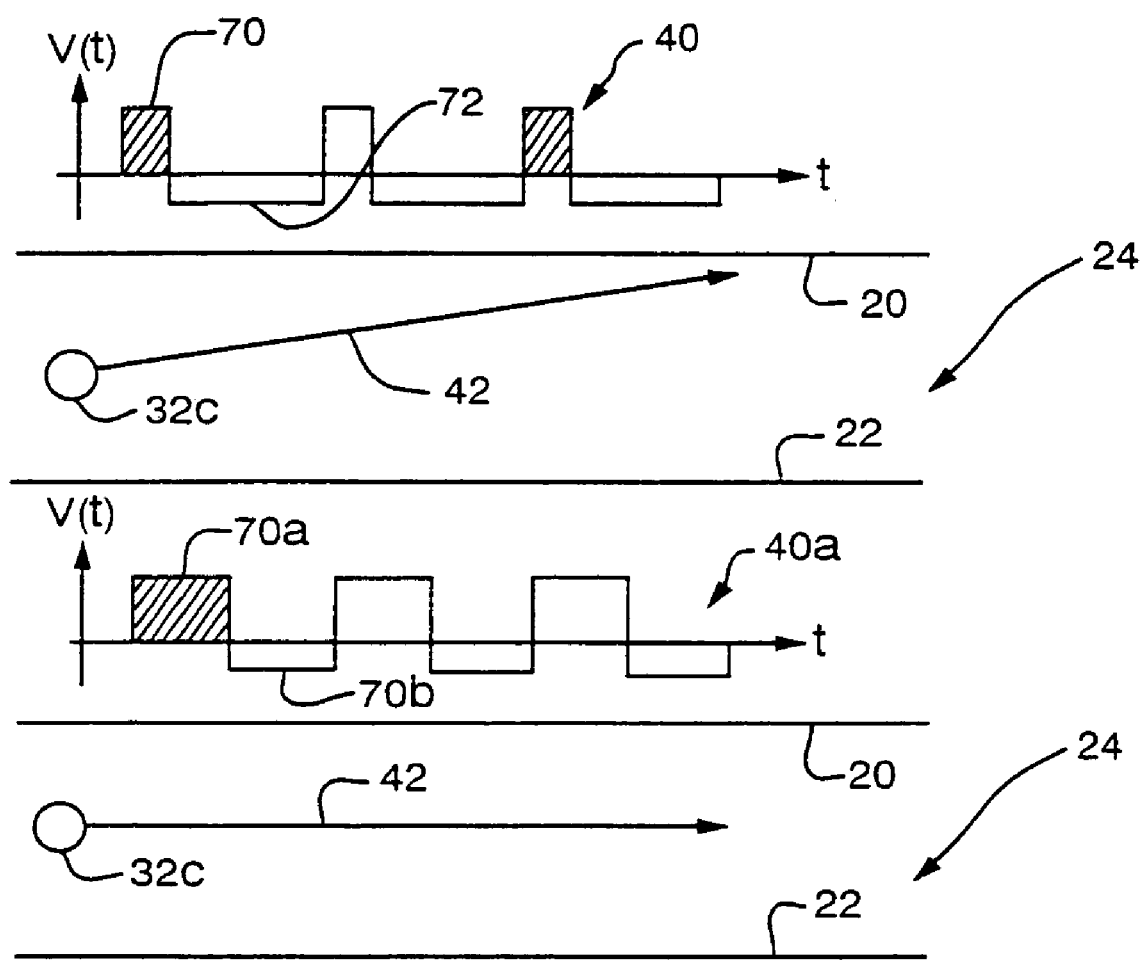
FIG. 11 is a graphical representation of an asymmetric periodic voltage having a varying duty cycle which is applied to the filter of FIG. 9 to filter selected ions without a bias voltage.

It has also been found that a compensation bias voltage is not necessary to detect a selected specie or species of ion. By varying the duty cycle of the asymmetric periodic voltage applied to electrodes 20 and 22 of filter 24, FIG. 10, there is no need to apply a constant bias voltage to plate electrodes 20 and 22. Voltage generator 28, in response to control electronics 30 varies the duty cycle of asymmetric alternating voltage 40. By varying the duty cycle of periodic voltage 40, FIG. 11, the path of selected ion 32c may be controlled. As an example, rather than a limitation, the duty cycle of field 40 may be one quarter: 25% high, peak 70, and 75% low, valley 72, and ion 38c approaches plate 20 to be neutralized. However, by varying the duty cycle of voltage 40a to 40%, peak 70a, ion 38c passes through plates 20 and 22 without being neutralized. Typically the duty cycle is variable from 10–50% high and 90–50% low. Accordingly, by varying the duty cycle of field 40, an ion's path may be controlled without the need of a bias voltage.

Figure 12:
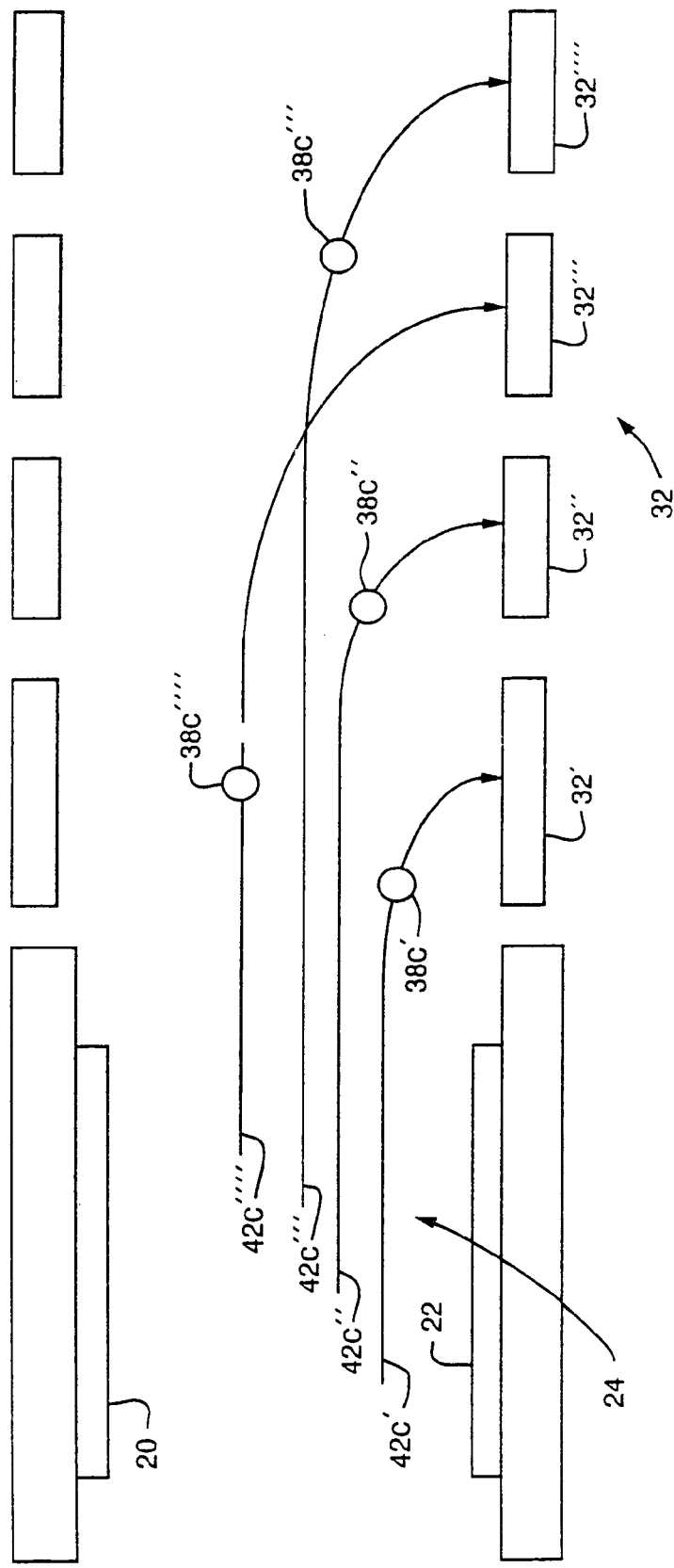
FIG. 12 is a schematic diagram of a filter and detector system in which the detector is segmented to spatially detect ions as they exit the filter.

To improve FAIM spectrometry resolution even further, detector 32, FIG. 12, may be segmented. Thus as ions pass through filter 24 between filter electrodes 20 and 22, the individual ions 38c'–38c'''' may be detected spatially, the ions having their trajectories 42'–42''' determined according to their size, charge and cross section. Thus detector segment 32' will have one a concentration of one species of ion while detector segment 32'' will have a different ion species concentration, increasing the spectrum resolution as each segment may detect a particular ion species.

Although specific features of the invention are shown in some drawings and not in others, this is for convenience only as each feature may be combined with any or all of the other features in accordance with the invention.

Other embodiments will occur to those skilled in the art and are within the following claims:

While this invention has been particularly shown and described with references to preferred embodiments thereof, it will be understood by those skilled in the art that various changes in form and details may be made therein without departing from the scope of the invention encompassed by the appended claims.

What is claimed is:

1. A system for analyzing a sample comprising,
   an asymmetric electric field for dispersing ions of the sample,
   an ion filter having filter electrodes separated by an analytical gap and defining a flow path, within which the asymmetric field is formed, and
   a controller for automatically adjusting at least one condition of the asymmetric field and at least one condition of the flow path to separate particular ones of the dispersed ions from others of the dispersed ions for analyzing a component in the sample.

2. The system of claim 1 comprising a control input for enabling an operator to selectively adjust the condition.

3. The system of claim 1 including a spectral detector for providing spectral information, at least about the separated ions, for analyzing the component in the sample.

4. The system of claim 3 including an input for taking into consideration changes in humidity in a flow path of the sample.

5. The system of claim 4, wherein the input takes into consideration changes in the spectral information due to the changes in the humidity.

6. The system of claim 3 wherein the controller takes into consideration changes in humidity in the flow path of the sample.

7. The system of claim 1 including a humidity sensor for measuring humidity in the flow path.

8. The system of claim 5, wherein analyzing the component includes measuring a quantity of the component in the sample.

9. The system of claim 1, where in the component includes moisture content of the sample and the analysis includes determining the moisture content of the sample.

10. The system of claim 1, wherein the component includes a chemical agent.

11. The system of claim 1, wherein the component includes an explosive agent.

12. The system of claim 1, wherein the component includes a drug.

13. The system of claim 1, wherein the component includes a biological agent.

14. The system of claim 1, wherein the sample includes air and analysis includes analyzing air quality.

15. The system of claim 1, wherein the at least one condition includes a DC bias voltage applied to a filter electrode to bias the asymmetric field or the amount of time that the DC bias voltage is applied to a filter electrode to control an amount of charge collected on a detector in the flow path.

16. The system of claim 1, wherein the at least one condition includes a duty cycle of the periodic voltage applied to the filter electrodes.

17. The system of claim 16, wherein the duty cycle is varied from about 10% to about 50% low.

18. The system of claim 1 including a longitudinally extending spacer in the ion filter for spacing apart at least two of the filter electrodes.

19. The system of claim 1 including a spacer plate for spacing apart at least two of the ion filter electrodes.

20. The system of claim 1 including an electrically conductive spacer for spacing apart at least two of the ion filter electrodes.

21. The system of claim 1 including an electrically insulative spacer for spacing apart at least two of the ion filter electrodes.

22. The system of claim 1 including an electrode for confining an ion travel path as the ions pass through the ion filter.

23. The system of claim 1 including at least two electrodes having differing applied biasing voltages, at least one of the electrodes acting as a confining electrode.

24. The system of claim 1 including an electrode for confining the ions to a substantially central portion of the flow path.

25. The system of claim 1 including at least two filter electrodes and at least two electrodes for directing travel of the particular ones of the ions along the flow path.

26. The system of claim 1, wherein the flow path is segmented to detect spatially the ions according to their trajectories.

27. The system of claim 3, wherein the spectral detector is segmented to detect spatially the ions according to their respective trajectories.

28. The system of claim 1, wherein the at least one condition includes an amount of heating or ion flow rate in the ion flow path.

29. The system of claim 1 including a doping inlet.

30. The system of claim 1, wherein the ion filter includes an array of filter electrodes.

31. The system of claim 30, wherein at least one electrode of the array of filter electrodes has an associated bias voltage different from a bias voltage associated with others of the filter electrodes.

32. The system of claim 1, wherein the ion filter includes at least two filters in the ion flow path.

33. The system of claim 1, wherein the filter electrodes are formed on opposing substrates.

34. The system of claim 33, wherein the substrates are substantially planar.

35. The system of claim 1, comprising a dopant inlet for introducing a dopant into a flow of a sample gas to change a spectrum of the component in the sample.

36. The system of claim 35, wherein the dopant includes acetone.

37. The system of claim 35, wherein the dopant includes water.

38. The system of claim 35, wherein the sample includes benzene.

39. The system of claim 35, wherein the dopant causes a shift in the spectrum.

40. The system of claim 35, wherein the at least one condition includes the amount of the dopant causing a change in an intensity level occurring in the spectrum.

41. The system of claim 35, including a display for displaying a plurality of spectra taken under different dopant conditions.

42. The system of claim 1, including multiple paths for ion species to have different ion species concentrations at different spatial locations.

43. The system of claim 1, including a plurality of ionization sources, a plurality of dopant inlets, and a plurality of outlets.

44. A method for analyzing a sample, comprising:
dispersing ions of the sample using an asymmetric electric field in a flow path, and automatically adjusting at least one condition of the asymmetric electric field and at least one condition of the flow path to separate particular ones of the dispersed ions from others of the dispersed ions.

45. The method of claim 44 including forming the asymmetric field in an analytical gap of filter electrodes.

46. The method of claim 44 comprising enabling an operator to selectively adjust the at least one condition.

47. The method of claim 44 including detecting spectral information, at least about the separated ions, for analyzing a component in the sample.

48. The method of claim 47 including taking into consideration changes in the spectral information due to changes in humidity in the flow path of the sample when analyzing the component in the sample.

49. The method of claim 47 wherein analyzing the component includes measuring the component in the sample.

50. The method of claim 47, where in the component includes moisture content of the sample.

51. The method of claim 47, wherein the component includes a chemical agent.

52. The method of claim 47, wherein the component includes an explosive agent.

53. The method of claim 47, wherein the component includes a drug.

54. The method of claim 47, wherein the component includes a biological agent.

55. The method of claim 47, wherein the at least one condition includes the amount of time that a bias voltage is applied to at least on filter electrode to control an amount of charge collected on a spectral detector in the flow path.

56. The method of claim 44, wherein the asymmetric field includes an RF field.

57. The method of claim 44, wherein the at least one condition includes a duty cycle of a periodic voltage applied to a ion filter to control the asymmetric electric field.

58. The method of claim 57, wherein the duty cycle is varied from about 10% to about 50% low.

59. The method of claim 44, wherein the at least one condition includes a bias applied to the asymmetric field to separate particular ones of the dispersed ions from others of the dispersed ions or an amount of electrical current applied to an ion filter to control the the amount of molecules that collect on the ion filter electrodes in the flow path.

60. The method of claim 44 including confining an ion travel path during the dispersing.

61. The method of claim 44, wherein the at least one condition includes a bias voltage level applied to a confining electrode to confine ions to a substantially central flow in the flow path.

62. The method of claim 44 including directing travel of the particular ones of the ions along the flow path.

63. The method of claim 44 including segmenting the flow path to detect spatially the ions according to their trajectories.

64. The method of claim 44, wherein the at least one condition includes an amount of heating or ion flow rate in the ion flow path.

65. The method of claim 44, wherein the at least one condition includes an amount of purified air in the ion flow path.

66. The method of claim 44, wherein the at least one condition includes an amount of a dopant in the flow path to change a spectrum associated with a component in the sample.

67. The method of claim 44, including the step of introducing a dopant into an ion flow path to change a spectrum associated with a component in the sample.

68. The method of claim 44, including the step of introducing a dopant into an ion flow path to change a compensation voltage associated with a component being detected in the sample.

69. The method of claim 66, wherein the dopant includes acetone.

70. The method of claim 66, wherein the dopant includes water.

71. The method of claim 66, wherein the component includes benzene.

72. The method of claim 66, wherein introducing the dopant causes a controlled shift in a spectrum associated with the component of the sample.

73. The method of claim 72, wherein the controlled shift includes shifting special peaks in the spectrum associated with the component of the sample.

74. The method of claim 66, wherein introducing the dopant causes a change in an intensity level associated with the component of the sample.

75. The method of claim 66, including providing multiple paths for ions to achieve different ion species concentrations at different spatial locations.

76. The method of claim 66, including comparing a spectrum of a component in a flow having an introduced dopant to a spectrum of a component without an introduced dopant.

77. The method of claim 44, wherein the at least one condition includes an amount of a gas other than air in the ion flow path.

78. The method of claim 77, wherein introducing a gas other than air causes a controlled shift in a spectrum associated with the component of the sample.

79. The method according to claim 78, wherein the controlled shift includes shifting special peaks in the spectrum associated with the component of the sample.

80. The method of claim 77, wherein the gas includes acetone.

81. The method of claim 77, wherein the gas includes benzene.

82. The method of claim 77, wherein the gas includes diethyl methyl amine.

83. The method of claim 44, wherein the at least one condition includes an amount of a mixture of gases other than air into in the ion flow path.

84. The method of claim 83, wherein introducing the mixture of gasses other than air causes a controlled shift in a spectrum associated with the component of the sample.

85. The method of claim 84, wherein the controlled shift includes shifting special peaks in the spectrum associated with the component of the sample.

86. The method of claim 83, wherein the mixture includes benzene and acetone.

87. The method of claim 44, wherein the at least one condition includes a mixture of vapors in the ion flow path.

88. The method of claim 87, wherein introducing the mixture of vapors causes a controlled shift in a spectrum associated with the component of the sample.

89. The method of claim 84, wherein the controlled shift includes shifting spectral peaks in the spectrum associated with the component of the sample.

90. The system of claim 1, wherein the at least one condition includes an amount of clean dry air in the ion flow path.

91. The system of claim 1, wherein the at least one condition includes an amount of one or more gases other than air in the ion flow path.

* * * * *